United States Patent [19]

Ghyczy et al.

[11] Patent Number: 4,506,831
[45] Date of Patent: Mar. 26, 1985

[54] PROCESS FOR THE SPRAY APPLICATION OF PLANT PROTECTIVE SPRAY MIXTURES AND PACKING UNITS FOR CONCENTRATES

[75] Inventors: Miklos Ghyczy, Cologne; Paul-Robert Imberge, Pulheim; Armin Wendel, Cologne, all of Fed. Rep. of Germany

[73] Assignee: Nattermann & Cie GmbH, Fed. Rep. of Germany

[21] Appl. No.: 508,663

[22] Filed: Jun. 28, 1983

[30] Foreign Application Priority Data

Jul. 9, 1982 [DE] Fed. Rep. of Germany ....... 3225705

[51] Int. Cl.³ .................. A01N 25/30; B65D 85/00
[52] U.S. Cl. .................................. 239/10; 71/64.08; 206/524.1
[58] Field of Search ............. 71/64.08, 64.13, DIG. 2; 239/1, 8, 10; 206/568, 538, 540, 524.1; 424/199

[56] References Cited

U.S. PATENT DOCUMENTS 2,006,227 6/1935 Bousquet ........................ 424/199
4,238,072 12/1980 Licursi ............................. 239/1

FOREIGN PATENT DOCUMENTS 68294 5/1983 European Pat. Off. .
68297 5/1983 European Pat. Off. .
944229 12/1963 United Kingdom .

Primary Examiner—Andres Kashnikow
Attorney, Agent, or Firm—Keil & Weinkauf

[57] ABSTRACT

Process for the application of plant protectant spray mixtures in which the phospholipid concentrates are applied to open ground, phospholipids being discharged along with commercially available, diluted effective ingredient concentrates and the spray mixtures being formed before discharge from the active ingredient concentrate, water, and the phospholipid concentrate. This process employs packing units which contain the active ingredient concentrate and the appropriate quantity of phospholipid concentrate in separate compartments.

16 Claims, No Drawings

PROCESS FOR THE SPRAY APPLICATION OF PLANT PROTECTIVE SPRAY MIXTURES AND PACKING UNITS FOR CONCENTRATES

The invention concerns a new process for the application of plant protective sprays for spraying on open ground, particularly on areas under agricultural use or fallow land, or open land on which plant growth is regulated in special fashion or on which parasites are to be combatted.

The invention also concerns packing units which contain the effective ingredient concentrate and phospholipide concentrate in separate containers.

Effective ingredient compositions consisting of herbicides, fungicides, insecticides, nematocides, or acaricides in combination with phospholipids in addition to conventional carrying agents, diluting agents, solvents, and/or other inactive ingredients are described in German patent applications P 31 25 423.3, P 31 25 399.7, P 31 25 422.5, P 31 25 448.9, and P 31 25 447.0. Plant protectant suspension concentrates consisting of insoluble or poorly soluble pesticides with a melting point of greater than 40° C., a phospholipid, and an organic solvent or solvent mixture are described in German patent application P 31 50 990.8.

Patent application WO 80/02360 describes how agricultural chemicals are to be applied, along with additives, to the surface in need of treatment, so as to improve the effect. Serving as additives are film formers which fix the effective substance on the plants, and quantities of surface-active substances which change the physico-chemical structure of the cells on the surface of the plants. Suitable surface-active substances are condensation products of alkylene oxide with fatty alcohols, amines, partial esters of long-chained fatty acids with glycerin, sorbitan, sugars, pentaerythritol, and the unconverted reaction partners of alkylene oxide, sodium and calcium salts of polyacrylic acids and lignosulfonic acide, and countless other substances, including lecithin.

DE-OS 29 07 303 and US-PS 4 241 046 describe a process for the casing of biologically active substances in synthetic, poligo-lamellar lipid vesicles (synthetic liposomes), in which process a phospholipid solution is mixed with an organic solvent and a watery preparation of the substance to be encased and is then emulsified into a W/O emulsion. After removing the organic solvent, a viscous gel arises, which is suspended in water. Pesticides are among the biologically active substances mentioned. The disadvantage of this process is that only aqueous preparations of biologically active substances can be encased, the process involves an expensive technique, and the gels obtained after vaporization of the organic solvent are limited with respect to storage. For its use with conventional commercial effective substance concentrations the process is not usable at all. In the form of the suspended gels the encased active substances cannot, for reasons of cost and durability, be placed on the market as agricultural chemical products.

Due their simple handling in transport, storage, and application as effective substance concentrates, plant protectants against parasites and weeds are today used commercially in the form emulsions (EC), suspensions (SC), solutions (LC), or easily moistened powders (WP), and are usually applied in liquid form, e.g. as solutions, suspensions or emulsions. The concentrates are diluted with the prescribed quantity of water before being applied or are moistened, and are then sprayed by means of conventional equipment in the form of spray mixtures from the ground or from the air (airplane or helicopter).

Most spray mixtures are disadvantaged by the fact that the known spraying equipment produces such small droplets that the resulting mist can be deflected by the wind, so that the intended agricultural areas are not adequately covered and additional areas sprayed as well.

Also known is the indirect drift of applied agents, which partially evaporate due to their volatility and are driven into neighboring areas due to the exchange of air masses with the wind. Depending on the volatility of the preparations, higher dosages are needed to assure that sufficient quantities of the effective substances fall on the intended areas. This represents an unnecessary environmental load, and damage is frequently done by the substance to the vegetation and animal life of the sprayed area, so that necessary spraying cannot be performed at the correct time due to unfavorable climatic conditions.

It is known in principle that the drift of sprayed mist can be reduced by increasing the droplet size. In their publication "Water-in-oil Emulsions and the Control of Spray Drift" (SCI Monograph No. 21, p. 47 ff, Soc. Chem. Ind. 1966, London) Colthurst and his colleagues describe the process in which stable droplets, whose size is not appreciably reduced after leaving the discharge nozzle, can be produced when water-in-oil emulsions are produced with a special nozzle, described in GB-PS 944 229. This device is formed in such a way that the oil and water phases are combined and emulsified in a small mixing chamber immediately in front of the nozzle. The structural design of the discharger, however, requires that the effective substance be specially formulated, the oil phase, solvent, and emulsifier being selected in such a way that a W/O emulsion resistant to the shearing load in the nozzle can form in the mixing chamber in the available time.

Effective substances in the form of liquid, easily diluted concentrates or as easily moistened powder are formulated by the manufacturer of the effective substances, who indicate on the packing and in their brochures the ratio in which the concentrate can be diluted or moistened with water to bring about the intended effect after spraying on the plants and ground. The form of application recommended by Colthurst, namely as W/O emulsion, has the drawback that a special application device is necessary and that additional special formulations are needed to produce stable W/O emulsions.

The encasing process described in DE-OS 29 07 303 cannot be employed as preliminary step in the application of spray mixtures.

There is, therefore, an urgent need for an application process that requires neither special devices nor the adaptation of the formulations to special mixing and application devices.

The objective of the invention is to create a suitable packing unit for the active ingredients and a process for the application of plant protectant spray mixtures, which process permits the use of known and obtainable active ingredient concentrates, the application being performed in such a way that sufficiently large and stable droplets are produced for the spray mist drift to be considerably reduced when the spray is discharged on open land.

This objective is achieved with a process for the discharge on open land of plant protectant spray mixtures containing phospholipids, in the form of spray mist, with a droplet size which prevents undesired drift, in which process known commercial active ingredient concentrates and phospholipid concentrates are diluted with water to form spray mixtures and the diluted mixtures are mixed together before spraying. It is also possible to directly mix the phospholipid concentrate with the plant protectant spray mixture. In a further form of the invention process the known commercial effective ingredient concentrate is first mixed with a phospholipid concentrate and then diluted with water to form a spray mixture.

Prefered forms of the invention process are described in the secondary claims.

The invention includes appropriate packing units.

The known commercial effective ingredient concentrates are first diluted with the appropriate quantity of water, in accordance with the manufacturer's specifications, or are moistened with water in the case of powders, to produce emulsions or suspensions of the active ingredient. A phospholipid concentrate is then added to these spray mixtures in the form of a concentrate, or in diluted form, thus producing the spray mixture for application. The phospholipid concentrate can be added in the usual mixing containers or in the container containing the known diluted spray mixture. The introduction of the phospholipid concentrate into the effective ingredient concentrates, which have been diluted to form the water spray mixtures, is preferably performed in so-called static mixers. In conducting the procedure there are two containers for diluting the concentrates with water. The container with the active ingredient emulsion or suspension and the container with the diluted phospholipid concentrate are connnected by means of connecting channels and a pump system, in such a way that the liquids can be separately conducted to a mixing nozzle, where the discharge spray is produced, to then be discharged by means of conventional spraying devices.

An advantage of the invention process is that the quantity of the effective ingredient expended can be reduced by 30 to 50%, in some cases even as much as 80%, since the use of phospholipids in spraying provides a much better distribution, even though the portion of very fine droplets is considerably reduced. Moistening of the plants and the ground is improved, thus increasing the selectivity and activity of the effective ingredient. The reduction of the spray mist droplet size after leaving the nozzle is impeded by the presence of phospholipids due to the delayed evaporation of considerable portions of liquid in the droplets.

The active ingredients are plant protectants in conventional solution, emulsion, suspension concentrates or are powders to be moistened, containing herbicidal, fungicidal, insecticidal, acaricidal, or nematocidal active ingredients.

The phospholipids employed are natural or synthetic phospholipids from the group of phosphatidyl choline, the hydrogenated phosphatidyl cholines, phosphatidyl ethanol amines, the N-acyl phosphatidyl ethanol amines, phosphatidyl inositol, phosphatidyl serine, and phosphatidyl glycerol, or a mixture of several such phospholipids, such as mixtures of phosphatidyl choline and phosphatidyl ethanol amine or phosphatidyl choline and phosphatidyl ethanol amine and N-acyl phosphatidyl ethanol amine, or other phosphatidyl choline mixture with phosphtidyl choline portions of from 20 to 98%. Especially preferred are natural phosphatidyl cholines, which can be obtained from processes described in the following patents: DE-PS 10 47 597, DE-PS 10 53 299, DE-PS 16 17 679, DE-PS 16 17 680, German patent applications DE-OS 30 47 048, DE-OS 30 47 012, or DE-OS 30 47 011.

Of the N-acyl phosphatidyl ethanol amines, those especially are recommended in which the acyl group is derived from saturated or olefinic unsaturated fatty acids with 2 to 20 carbon atoms, particularly saturated fatty acids with 2 to 5 carbon atoms or saturated or olefinic unsaturated fatty acids with 14, 16, 18, or 20 carbon acids.

In order to produce liquid preparations the phospholipids are added to physiologically acceptable organic solvents or solvent mixtures, such as alcohol or ether, e.g. methanol, ethanol, propanol, isopropanol, butanol, isobutanol, tert. butanol, sec. butanol, ethylene gylcol, ethylene gylcol monoethyl ether, ethylene glycol dimethyl ether, ethylene glycol diethyl ether, diethylene gylcol monomethyl ether, diethylene gylcol monoethyl ether, diethylene glycol monomethyl ether, diethylene glycol propyl ether, diethylene glycol diethyl ether, polyethylene glycol, propylene gylcols, polpylene glycol monomethyl ether, propylene glycol monoethyl ether, propylene glycoldimethyl ether, propylene glycol deithyl ether, butylene gylcol, glycerin, solcetal, tetrahydrofurane, isophorone, dioxane, dimethyl sulfoxide; natural oils can also be used, e.g. soy oil.

Preferred are mixtures of isophoron, gylcerin, and, as the need arises, $C_1$–$C_3$ alcohols.

The phospholipid concentrates usually have a concentration of from 20 to 60 weight % to assure that they can be easily managed and pumped.

Along with the phospholipids and solvents serving as carrier liquids, the phospholipid concentrates contain a co-emulsifier and a solute, and if necessary further suitable additives, such as vegetable oils or small quantities of water. Non-ionogenic products are particularly suitable as co-emulsifiers, for example the products marketed under the trade-name Cremophor, which are ethoxylates of fatty alcohols or hydrogenated castor oils or nonyl phenol or fatty acid amides.

The solutes used can be commercial products such Tween, Softigen, Span Miglyol, Marlowet, and the like. These are sorbitan fatty acid esters, triglyceride or partial gylceride mixtures of saturated vegetable fatty acids, or hydroxyethyl amides, e.g. N-(2-hydroxyethyl)-caproic acid amide.

To achieve the intended effect in the production of the discharged spray mixtures and in the application process itself, the quantity of the phospholipid concentrate added is such as to create an active ingredient: phospholipid ratio in the ultimate spray mixture of from 1:0.5 to 1:5. The preferable ratio is from 1:1 to 1:2.

The manufacturer's specifications on the active ingredient concentrates make it possible to select without difficulty the quantity of phospholipid concentrate necessary to create the above named ratio of active ingredient to phospholipid.

Preferably, however, the plant protectant will be packed in combination packages with the phospholipid concentrates, each in separate containers, so that the correct concentration ratio for the given active ingredient is established by the manufacturer and errors performed in diluting process by less skilled users can be larged eliminated.

Such combination packages might have two separately sealed filling spaces within one container. Depending on the structure of the package, the contents could be removed separately, to be placed in separate preparation containers in the spraying device, or removed together, to be mixed and introduced into the dilution and storage compartment of the spraying device, in which the final concentration is created by means of dilution with water. The combination package can also be designed so that two separate containers are arranged in an outer package, with wall material that is soluble in water or will disintegrate in water, enabling the containers to be placed in the mixing and storage compartment and filled with the appropriate quantity of water, without being opened before hand.

Examples of phospholipid concentrates suitable for the invention process and the combination package have the following composition:

1.
  40 wght. % phospholipids
  35 wght. % isophorone (3,5,5-trimethyl-2-cyclohexene-1-on)
  14 wght. % glycerin
  5 wght. % co-emulsifier
  5 wght. % dissolving intermediary
2.
  25 wght. % phospholipids
  45 wght. % isophorone
  22.5 wght. % glycerin
  7.5 wght. % co-emulsifier
3.
  35 wght. % phosopholipids
  25 wght. % neutral oil (tri-glyceride mixture of saturated vegetable fatty acids)
  35 wght. % dissolving intermediary
  5 wght. % methanol
4.
  26.6 wght. % phospholipids
  10 wght. % glycerin
  23.4 wght. % isophorone
  3.3 wght. % co-emulsifier
  3.3 wght. % dissolving intermediary
  13.4 wght. % water
  20 wght. % vegetable oil
5.
  26.6 wght. % phospholipids
  10 wght. % glycerin
  23.4 wght. % isophorone
  20 wght. % neutral oil
  3.3 wght. % co-emulsifier
  3.3 wght. % dissolving intermediary
  13.4 wght. % water
6.
  32 wght. % phospholipids
  15 wght. % glycerin
  35 wght. % isophorone
  5 wght. % co-emulsifier
  5 wght. % dissolving intermediary
  8 wght. % ethanol
7.
  53.4 wght. % phospholipids
  11.1 wght. % acetic ester
  11.1 wght. % n-butanol
  11.1 wght. % glycerin
  13.3 wght. % ethanol
8.
  48 wght. % phospholipids
  33.3 wght. % isopropanol
  12 wght. % ethanol
  6.7 wght. % water
9.
  37.5 wght. % phospholipids
  34.4 wght. % methanol
  28.1 wght. % ethylene glycol ethyl ether
10.
  40 wght. % phospholipids
  15 wght. % glycerin
  35 wght. % co-emulsifier
  5 wght. % dissolving intermediary.

The invention process for combination with phospholipids for the purpose of spraying has proven to be particularly effective for the following active ingredients:

| conventional designation of active ingredient | concentrate form | mg/l active ingredient in spray mixture |
| --- | --- | --- |
| fungicides | | |
| triadimefon | spray powder | 250 |
| copper oxychloride | wettable powder | 1350 |
| propineb | wettable powder | 1400 |
| procymidone | wettable powder | 375 |
| wettable sulfur | wettable powder | 2000 |
| herbicides | | |
| glyphosat | aqueous solution | 4800 |
| linuron | spray powder | 1763 |
| terbuthylazin | suspension | 10,000 |
| flampropisopropyl | emulsion | 1750 |
| trifluralin | emulsion | 3216 |
| dinoseb-acetate | emulsion | 4920 |
| chlormequatchlorid | aqueous solution | 7800 |
| chloridazon | suspension | 6450 |
| isoproturon | wettable powder | 5025 |
| alloxydim-Na | soluble powder | 6563 |
| atrazin | wettable powder | 3600 |
| insecticides | | |
| malthion | emulsion | 20,400 |
| propoxur | emulsion | 400 |
| permethrin | emulsion | 225 |
| cypermethrin | emulsion | 240 |
| heptenophos | emulsion | 1000 |

EXAMPLE 1

An initial spray mixture is produced with water from a commercially available spray powder with 25% triadimefon as active ingredient; the spray mixture contains 250 mg/l of active ingredient.

A second spray mixture, containing 250 mg/l phospholipid, is prepared with water from a phospholipid concentrate of the above indicated compound no. 1.

The two spray mixtures are fed from two identical tanks through a static mixer and homogenized, to be sprayed in the usual fashion. The spray mixture can be discharged easily, and a droplet size can be set in which only a small portion of the droplets is smaller than 200 micrometers.

EXAMPLE 2

Using the spray mixture produced as indicated in example 1 containing 250 mg/l of triadimefon, the phospholipid concentrate of compound no. 2 indicated above is stirred in directly and in a quantity such the resulting mixture contains 250 mg/l phospholipid; the mixture is stirred for a short time, and the resulting spray mixture can be discharged in the usual fashion. The spray mixture can be discharged successfully with the usual equipment, and it is possible to adjust the droplet size so that only a small portion of the droplets have a size smaller than about 20 micrometers.

EXAMPLE 3

A packing unit contains a concentrated aqueous solution of glyphosat and a phospholipid concentrate of compound 2 in separate compartments and in quantities such that the final spray mixture contains herbicide and phospholipids in a ratio of 1:1. The two concentrates are combined, diluted with water, stirred, and homogenized to form a spray mixture that contains 4800 mg/l of herbicide and phospholipids.

The spray mixture can be easily sprayed with the usual equipment, in the form of a spray mist.

EXAMPLE 4

A packing unit contains a concentrated emulsion of trifluralin and a phospholipid concentrate of compounded 6 in separate compartments and in quantities such that the final spray mixture contains herbicide and phospholipids in a ratio of 1:2. The two concentrates are diluted with water to form spray mixtures with contents of 3216 mg/l and 6432 mg/l and are introduced from separate containers into a mixing nozzle and combined to form a homogeneous spray mixture, which can then be discharged as a spray mist. It was possible to produce a homogeneous spray mixture without difficulty by means of a conventional mixing nozzle, and the resulting spray mixture was easy to apply.

EXAMPLE 5

A commercially available emulsion of the insecticide malathion was diluted with water according to the manufacturer's instructions, to form a spray mixture with a content of 20,400 mg/l. A phospholipid concentrate of compound no. 4 for was added to the spray mixture in a quantity such that the ratio of insecticide to phospholipid was 1:0.5. The mixture was stirred in a container with a mixer. The resulting spray mixture can be easily atomized in conventional equipment, with only a small portion of droplets having a size less than 200 micrometers. A low degree of drift is therefore present during application.

Further experiments established that the above mentioned plant protectants, with suitable phospholipid concentrates of various composition, can be successfully converted with the invention procedure into spray mixtures that are easily applied, with mixing and discharge performed by conventional equipment. The specialist will have no difficulty in selecting the phospholipid concentrate that provides an optimum spray mixture. To facilitate the selection, active ingredient concentrate and phospholipid concentrate are best provided in packing units containing the appropriate concentrate quantities and compositions. Mixing, dilution, and discharge can be performed with the usual devices. Spray mist with only a small portion of droplets smaller than 200 micrometers can be produced; the droplet size diminishes only slightly as the spray mists falls to the ground, since the phospholipid stabilizes the droplet size. With the invention process not only is the spray mist drift reduced during discharge, but the indirect drift of the applied active ingredients is also reduced, as described, for example, in the Special Volume VII of the Journal for Plant Diseases and Plant Protection 1975 by G. Maas et al.

One special advantage of the invention process is that the application of phospholipid concentrates for the production of spray mixtures can utilize the usual existing devices without difficulty; the commercially available active ingredient formulations need not be modified to combine the phospholipid concentrations in the spray mixtures.

We claim:

1. Process for the discharge on open ground of plant protectant spray mixtures containing phospholipids in the form of spray mist, with droplet sizes which avoid undesirable drift, wherein commercially available active ingredient concentrates and phospholipid concentrates are first diluted with water to form spray mixtures and the diluted mixtures are mixed before spraying.

2. Process for the discharge on open land of plant protectant spray mixtures containing phospholipids, in the form of spray mist with droplets whose size prevents undesired drift, wherein commericially available active ingredient concentrates are first diluted with water, a phospholipid concentrate is added to the mixture, and a spray mixture is formed.

3. Process for the discharge on open land of plant protectant spray mixtures containing phospholipids, in the form of spray mixtures with droplets whose size prevents undesired drift, wherein the commercially available active ingredient concentrate is first mixed with a phospholipid concentrate and the mixture is then diluted with water to form a spray mixture.

4. A process as set forth in claim 2, wherein the diluted active ingredient concentrate and the phospholipid are introduced into a static mixer and a spray mixture is formed.

5. A process as set forth in claim 1, wherein the separate liquids are introduced into a mixing nozzle and a spray mixture is formed.

6. A process as set forth in claim 3, wherein the concentrates are combined from separate containers in a packing unit.

7. A process as set forth in claim 1, wherein the employed phospholipids are liquid preparations in a physiologically acceptable carrier liquid of one or several phospholipids from the group of phosphatidyl choline, the hydrogenated phosphatidyl cholines, phosphatidyl ethanolamine, the N-acylphosphatidyl ethanolamines, phosphatidyl inositol, phosphatidyl serine, lysolecithin, and phosphatidyl glycerol.

8. A process as set forth in claim 1, wherein the phospholipid employed is phosphatidyl choline or mixtures of phosphatidyl choline and phosphatidyl ethanolamine or mixtures of phosphatidyl choline/phosphatidyl ethanolamine and N-acyl phosphatidyl ethanolamine.

9. A process as set forth in claim 1, wherein the phospholipid employed is a phospholipid with a content of 20 to 98% phosphatidyl choline.

10. A process as set forth in claim 1, wherein the phospholipid concentrate employed contains 20 to 60 weight-% phospholipid, in relation to the concentrate, with solvents, co-emulsifiers, solutes, and other conventional additives.

11. A process as set forth in claim 1, wherein the quantity of phospholipid concentrate employed creates an active ingredient: phospholipid ratio of from 1:0.5 to 1:5, preferably from 1:1 to 1:2.

12. Packing unit for active ingredient concentrates, such as plant protectants, containing a commercially available active ingredient concentrate, wherein the packing unit contains the commercially available active ingredient concentrate and a phospholipid concentrate in separate spaces, the given quantities of active ingredient concentrate and phospholipid concentrate being such that in mixing the components before or after their dilution with water the desired spray mixture is created.

13. A packing unit for active ingredient concentrates as set forth in claim 12, wherein the phospholipid concentrate contained is a liquid preparation, in a physiologically acceptable carrier liquid, of one or several phospholipids from the group of phosphatidyl choline, the hydrogenated phosphatidyl cholines, phosphatidyl ethanolamine, the N-acyl phosphatidyl ethanolamines, phosphatidyl inositol, phosphatidyl serine, lysolecithin, and phosphatidyl glycerol.

14. A packing unit for active ingredient concentrates as set forth in claim 12, wherein the phospholipid contained is phosphatidyl choline or mixtures of phosphatidyl choline and phosphatidyl ethanolamine or mixtures of phosphatidyl choline/phosphatidyl ethanolamine and N-acylphosphatidyl ethanolamine.

15. A packing unit for active ingredient concentrates as set form in claim 12, wherein the weight ratio of active ingredient to phospholipid is from 1:0.5 to 1:5, preferably from 1:1 to 1:2.

16. A use of packing units for active ingredient concentrates, such as plant protectants, as set form in claim 12, for the production of spray mixtures by means of mixing with water before or after dilution and formation of a spray mixture.

* * * * *